United States Patent
Morimoto et al.

(10) Patent No.: US 6,489,369 B1
(45) Date of Patent: Dec. 3, 2002

(54) PHOSPHOCHOLINE SURFACTANTS AND THEIR USE

(75) Inventors: Bruce H. Morimoto, Redwood City, CA (US); Peter L. Barker, Pleasanton, CA (US); Vincent Hernandez, Brookdale, CA (US); Cass K. Piper, Redwood Shores, CA (US)

(73) Assignee: SuperGen, Inc., San Ramon, CA (US)

( * ) Notice: Subject to any disclaimer, the term of this patent is extended or adjusted under 35 U.S.C. 154(b) by 0 days.

(21) Appl. No.: 09/493,359

(22) Filed: Jan. 28, 2000

Related U.S. Application Data

(60) Provisional application No. 60/118,499, filed on Feb. 3, 1999.

(51) Int. Cl.$^7$ .................. A61K 31/685; A61K 31/56

(52) U.S. Cl. .................. 516/170; 514/171; 514/77; 514/78; 514/182

(58) Field of Search ................ 514/170, 171, 514/182, 77, 78

(56) References Cited

U.S. PATENT DOCUMENTS

| | | | |
|---|---|---|---|
| 5,703,063 A | 12/1997 | Chasalow | 514/78 |
| 5,776,915 A | 7/1998 | Peterson et al. | 514/77 |
| 5,804,569 A | 9/1998 | Peterson et al. | 514/77 |
| 5,888,990 A | 3/1999 | Chasalow | 514/78 |
| 6,017,904 A | 1/2000 | Reed et al. | 514/75 |

*Primary Examiner*—Sabiha Qazi
(74) *Attorney, Agent, or Firm*—Darby & Darby

(57) ABSTRACT

A pharmaceutical formulation comprising a pharmaceutically active agent, which is insoluble or sparingly soluble in water and a sterol phosphocholine surfactant.

13 Claims, No Drawings

PHOSPHOCHOLINE SURFACTANTS AND THEIR USE

This application claims the benefit of Provisional Application No. 60/118,499 filed Feb. 3, 1999.

FIELD OF THE INVENTION

This invention relates to novel detergents or surfactants based on amphipathic phosphocholine compounds to improve pharmaceutical formulations and their use as pharmaceutical excipients. Phosphocholine surfactants are used for the aqueous solubilization of active agents which are insoluble or sparingly soluble in water. Since phosphocholine is an endogenous component of cell membranes, these surfactants are expected to be biocompatible and biodegradable. Unlike many other surfactants, these phosphocholine surfactants are solid at room temperature and therefore have improved storage properties as dried powders or lyophilized formulations.

BACKGROUND OF THE INVENTION

There is a tremendous need for biodegradable and biocompatible surfactants in the pharmaceutical industry. Current surfactants used for parenteral delivery, often elicit an anaphylactoid reaction. Most surfacants are not composed of endogenous components; therefore, the body often recognizes these molecules as "foreign" and an immune response prevails. Phosphocholine is a natural zwitterionic component of all cell membranes. Surfactants composed of phosphocholine conjugated to a hydrophobic molecule would therefore be safe and biocompatible.

Parenteral delivery of insoluble or poorly soluble drugs is problematic. For example, intravenous administration of paclitaxel or cyclosporin A is accomplished by forming emulsions with Cremophor®EL. The poly(oxyethylene)-40-castor oil in Cremophor®EL can result in hypotension, dyspnea, angioedema, or generalized urticaria. These hypersensitive reactions can lead to life-threatening conditions, and it is recommended that all patients be premedicated with corticosteroids, diphenhydramine, and H2 antagonists to avoid severe hypersensitivity.

In another example, the anesthetic, propofol, is administered commercially as an emulsion containing soy bean oil, glycerol, and egg phosphatide. Microbial contamination is one of the greatest concerns with the current formulation of propofol, which can result in life-threatening illness or death from fever, infection or sepsis. This is especially problematic for post-operative or intensive care unit (ICU) patients. Although U.S. Pat. No. 5,714,520 discloses a method to minimize microbial contamination by the addition of the preservative edeate, this formulation is not an antimicrobial preserved product by USP standards and extrinsic contamination remains problematic.

Cyclodextrins are also used in increasing the solubility of a compound 100- to 1000-fold. This is the upper limit of their usefulness and is related to the thermodynamic equilibrium binding constant, which is $10^5$. Additionally, cyclodextrins are only useful in solubilizing compounds with low molecular weights, and the compound must be partially soluble (around 1 μg/ml).

U.S. Pat. No. 5,747,066 of Pittrof and Steffen describes the formation of mixed micelles for aqueous solubilization of active substances using phosphatides which are phospholipids comprised of glycerol, fatty acids, and phosphocholine. The critical micellar concentration (cmc) of phosphatides decreases as the length of the fatty acyl chain increases (Jones and Chapman, 1995), such that for all practical purposes, there is no appreciable concentration of monomeric species of natural membrane phosphatides with C16 to C18 acyl chains. While the use of phosphatides disclosed by Pittrof and Steffen is significant, phosphatides are large molecules and since they contain two fatty acyl chains in conjunction with a zwitterionic head group (phosphocholine), they form a variety of lyotropic mesophases in aqueous media. This potentially limits the ability of phospholipids, such as the phosphatides disclosed by Pittrof and Steffen, to solublize a wide variety of pharmaceutical agents. Moreover, these mixed micellar emulsions are meta-stable and precipitation or crystallization of the insoluble drug can occur, which when administered intravenously, can increase the risk of an embolism.

Methods for increasing the bioavailability of several steroid phosphocholine conjugates are disclosed in U.S. Pat. No. 5,703,063. The surfactant properties of one steroid phosphocholine conjugate, namely cholesterol-phosphocholine, is described by Lyte, M. et al. (1979) Chem. Phys. Lipids 24, 45–55 and Ayengar, N. K. N. et al. (1979) Chem. Phys. Lipids 25, 203–208.

Therefore, a need exists for new surfactants to solubilize pharmaceutical agents for various routes of administration. Additionally, biocompatible surfactants that will not cause adverse side effects, and could be used in the delivery of pharmaceutical agents representing a plethora of therapeutic areas, including, but not limited to, proteins, peptides, nucleic acids, and small molecule drugs.

SUMMARY OF THE INVENTION

This invention relates to novel amphipathic phosphocholine derivatives which function as biodegradable and biocompatible surfactants, and their use as excipients in pharmaceutical formulation.

It is an object of the present invention to provide compositions of matter which substantially increase the aqueous solubility of pharmaceutically active agents comprising a micellar or amorphous complex of a phosphocholine surfactant and the agent. The pharmaceutically active agent may include but not limited to, antibiotics, antifungal, antiviral, antineoplastic drugs, analgesics, and anesthetics. The most preferred agents are those which are insoluble or poorly soluble and administered intravascularly, such as etoposide, paclitaxel, propofol, and cyclosporin.

DETAILED DESCRIPTION OF THE INVENTION

All patent applications, patents and literature reference cited herein are hereby incorporated by reference in their entirety.

The present invention relates to the unexpected discovery that the intrinsic aqueous solubility of various phosphocholine-conjugates varies from 1 mg/ml to greater than 500 mg/ml. This range of solubility is due in part to the formation of unique hydrated micellar structures.

This invention also relates to the unexpected discovery that many phosphocholine conjugates of sterically hindered alcohols, such as secondary and tertiary alcohols or alcohols in which neighboring groups are within van der Waals radii of the alcohol are not rapidly hydrolyzed by serum enzymes; whereas, phosphocholine conjugates of primary and phenolic alcohols are susceptible to enzymatic cleavage. This discovery predicts that phosphocholine-conjugates can function as both biodegradable and biostable surfactants, depending on the chemical nature of the phosphocholine linkage. Non-limiting examples of such sterically hindered alcohols are steroid phosphocholines and cholesterol phosphocholine.

A phosphocholine surfactant is defined herein as a compound in which phosphocholine is attached to a hydrophobic molecule by the formation of a covalent phosphoester bond. Non-limiting examples of the hydrophobic molecule are one of a number of steroids, such as cholesterol; β-sitosterol[24-ethylcholesterol]; stigmasterol[3-hydroxy 24-ethyl 5,22-cholestadiene]; ergosterol[5,7,22 ergostatrien-3-ol]; 3,7,12-trihydroxy-5-cholane; 3,12-dihydroxy-5β-cholane; or aliphatic derivatives, such as dodecanol; tetradecanol; hexadecanol; octadecanol; eicosanol; docosanol; tetracosanol; 11-hexadecenol; 9-hexadecenol; 9-octadecenol; or 9,12-octadecadienol. These compounds can be purchased from numerous commercial sources such as Sigma Chemical Co. (St. Louis, Mo.), Aldrich Chemical Co. (Milwaukee, Wis.), Acros Chemicals (Pittsburgh, Pa.) or Fluka Chemical Corp. (Milwaukee, Wis.).

The solubility of a phosphocholine-conjugate is mediated by the formation of a hydrated micellar structure. Unlike liposomes which are metastable thermodynamic structures, micelles are self-associating and thermodynamically stable. Therefore, phosphocholine-based surfactants are potentially useful as new excipients. In addition to solubilization, phosphocholine-surfactants may also function as absorption enhancers by affecting membrane stability and/or disruption. Phosphocholine-surfactants also have the physical chemical property of being solid. This is an advantage over many current surfactants which are liquids or oils, since a pharmaceutical agent can be mixed with the phosphocholine-surfactant and then lyophlized to dryness for storage. The drug could then be reconstituted prior to administration. This would give rise to a more stable pharmaceutical formulation.

The present invention provides a means for improving the usefulness of any drug which suffers from poor aqueous solubility. The method of the invention is advantageously applicable to a variety of drugs. Examples of the variety of therapeutic classes of drugs that can be effectively solublized with phosphocholine surfactants include, but not limited to:

Anti-neoplastic agents, for example, paclitaxel and other taxanes, etoposide, vincristine, vinblastine, topisomerase I inhibitors such as camptothecin, irinoctecan (Pharmacia and Upjohn, Kalamazoo, Mich.), topothecan (Smith, Beecham, Philadelphia, Pa.), CPT11 (Bristol-Myers Squibb, Princeton, N.J.);

Antiviral agents, including nucleoside analogs and protease inhibitors, such as nelfinavir (Agouron, La Jolla, Calif.), Saquinavir (Roche, Nutley, N.J.), Crixivan (Merck West, Point, Pa.), Ritonavir (Abbott, N. Chicago, Ill.);

Antibiotics, particularly mitomycin, bleomycin, daunorubicin, doxorubicin, plicamycin, dactinomycin, and amphoteracin;

Anesthetics, such as propofol and barbituates, for use in general anesthesia or sedation;

Analgesics, such as morphine, codeine, and Ziconotide (Neurex Menlo Park, Calif.);

Therapeutic peptides or peptidomimetics, composed of D-amino acids, L-amino acids, or amino acid analogs, acting as enzyme inhibitors, receptor ligands, or disruptors of protein-protein interactions, such as cyclosporin A;

Therapeutic polypeptides or proteins, such as leptin, growth hormone, calicitonin, vasopressin, renin, prolactin, thyroid and parathyroid hormones, corticotropin, corticotropin-releasing factor, follicle stimulating hormone, luteinizing hormone, gonadotropin, atrial peptides, isolated from natural sources or produced by recombinant DNA technology;

Nucleic acids, such as anti-sense oligonucleotides or nucleic acids for gene therapy, composed of ribo- or deoxyribonucleotides or nucleotide analogs.

Unless otherwise specifically noted, the compounds described herein can be purchased from numerous commercial sources, such as Sigma Chemical Co. (St. Louis, Mo.) Calbiochem-Novabiochem (San Diego, Calif.), Research Biochemicals, Inc. (Natick, Mass.) or Alexis Corp. (San Diego, Calif.).

In one preferred embodiment, the phosphocholine surfactant is of the formula:

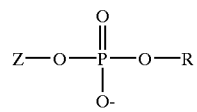

wherein R contains about 4 to 24 carbon atoms, may be saturated or unsaturated, and may be a straight chain aliphatic or branched chain aliphatic group; and Z is selected from the group consisting of choline, ethanolamine, N-methyl ethanolamine, N,N-dimethyl ethanolamine, serine, threonine or tyronine.

A particularly preferred compound of this type is

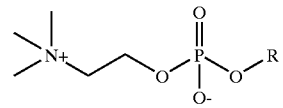

wherein R is the saturated fatty acid lauric, myristic, palmitic or stearic or the unsaturated fatty acid palmitoleic, oleic, linoleic or arachidonic.

In another preferred embodiment the phosphocholine surfactant is of the formula:

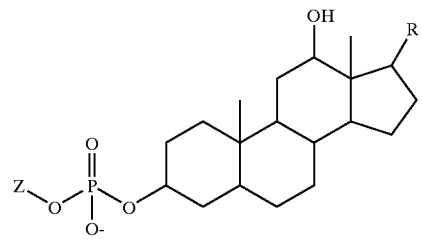

wherein R contains about 4 to 24 carbon atoms, may be saturated or unsaturated, and may be straight chain aliphatic or branched chain aliphatic group, including but not limited to, —CH(CH$_3$)—(CH$_2$)$_3$—CH(CH$_3$)$_2$; and Z is selected from the group consisting of choline, ethanolamine, N-methyl ethanolamine, N,N-dimethyl ethanolamine, serine, threonine, or tyronine.

A particularly preferred compound is

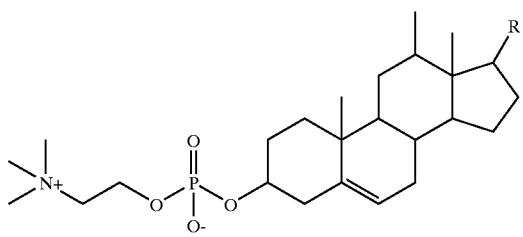

wherein R is H.

In yet another preferred embodiment the phosphocholine surfactant is of the formula:

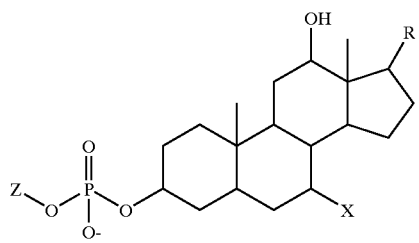

wherein R contains about 4 to 24 carbon atoms, may be saturated or unsaturated, and may be straight chain aliphatic or branched chain aliphatic group, including but not limited to, —CH(CH$_3$)—(CH$_2$)$_3$—CH(CH$_3$)$_2$, —CH(CH$_3$)—(CH$_2$)$_2$—CH(CH$_2$CH$_3$)—CH(CH$_3$)$_2$, or —CH(CH$_3$)—CH=CH—CH(CH$_2$CH$_3$)—CH(CH$_3$)$_2$; and Z is selected from the group consisting of choline, ethanolamine, N-methyl ethanolamine, N,N-dimethyl ethanolamine, serine, threonine, or tyrosine.

A particularly preferred compound is

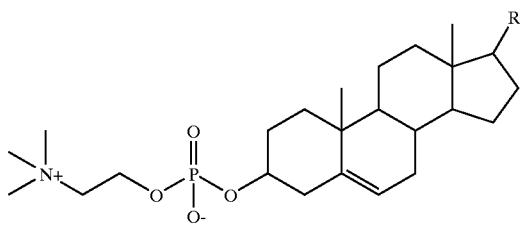

wherein R is —CH(CH$_3$)—CH=CH—CH(CH$_2$CH$_3$)—CH(CH$_3$)$_2$ or —CH(CH$_3$)—(CH$_2$)$_2$—CH(CH$_2$CH$_3$)—CH(CH$_3$)$_2$, corresponding to the structures of the steroids stigmasterol or β-sitosterol, respectively.

In another preferred embodiment the phosphocholine surfactant is of the formula:

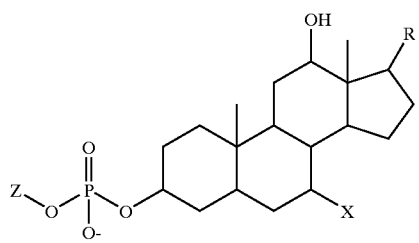

wherein R contains about 4 to 24 carbon atoms, may be saturated or unsaturated, and may be straight chain aliphatic or branched chain aliphatic group, and X=H or OH; and Z is selected from the group consisting of choline, ethanolamine, N-methyl ethanolamine, N,N-dimethyl ethanolamine, serine, threonine, or tyrosine.

A particularly preferred compound is

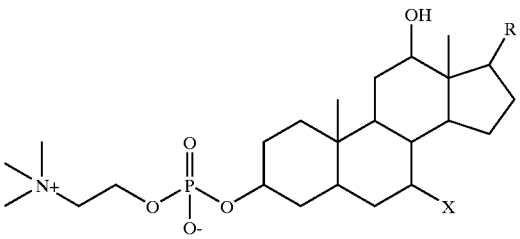

wherein
R is H;
X is H.

In another preferred embodiment the phosphocholine surfactant is of the formula:

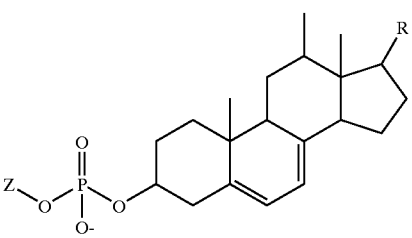

wherein R contains about 4 to 24 carbon atoms, may be saturated or unsaturated, and may be straight chain aliphatic or branched chain aliphatic group, including but not limited to, —CH(CH$_3$)—(CH$_2$)$_3$—CH(CH$_3$)$_2$, or —CH(CH$_3$)—CH=C(CH$_3$)—CH(CH$_3$)$_2$; and Z is selected from the group consisting of choline, ethanolamine, N-methyl ethanolamine, N,N-dimethyl ethanolamine, serine, threonine, or tyrosine.

A particularly preferred compound is

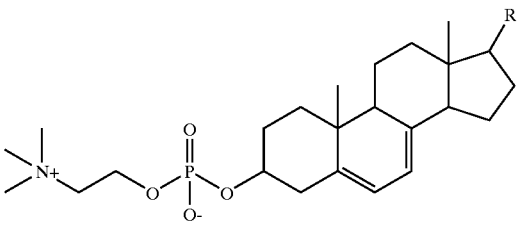

wherein R is —CH(CH$_3$)—CH=C(CH$_3$)—CH(CH$_3$)$_2$, corresponding to the steroid ergosterol.

As mentioned above, the compositions of matter of this invention comprise a pharmaceutically active agent and a phosphocholine surfactant. The relative amounts of agent and phosphocholine surfactant will vary depending on the chemical property of the agent, its relative solubility, and the effect of the surfactant on the agent. In general, the ratio of the weight of agent to the weight of the surfactant will be in a range between 1:1 to 1:10,000. A weight ratio in a range of 1:10 to 1:500 is most preferred as it is believed to be effective for the solubilization of a number of compounds.

The choice of the combination of surfactant/pharmaceutical agent and ratio can be determined by routine experimentation known to those in ordinary skill in the art. For example, a 10% (weight/volume) aqueous solution of each surfactant is made and various amounts are added to a known weight of the pharmaceutical agent and mixed. The final volume of the mixture is adjusted with water or saline so that the final concentration of the agent is appropriate for administration. The turbidity of the solution is measured by standard methods, such as light scattering or spectrophotometry. Mixtures with the least turbidity are those in which solubilization of the agent is optimal.

The compositions of matter according to this invention may be provided as a powder comprising the active agent and the surfactant. If the composition is to be administered parenterally, for example by intravenous route (IV), the composition of matter will be rendered sterile prior to such administration. Any of the several known means of rendering such pharmaceutical preparations sterile may be used.

The compositions of matter according to this invention may also be used in oral administration. If so, formulations can be in the form of tablets, capsules, pills, ampoules of powdered agent, or oily or aqueous suspensions or solutions. Tablets or other non-liquid oral compositions may contain acceptable excipients, vehicles, diluents, fragrances, or flavors known to the art for the manufacture of pharmaceutical compositions, to make the medication palatable or pleasing to use. The formulation can therefore also include diluents such as lactose or calcium carbonate; binding agents such as gelatin or starch; and one or more agents selected from the group consisting of sweetening agents, flavoring agents, coloring, or preserving agents. Moreover, such oral preparations may be coated by known techniques to further delay disintegration and absorption in the intestinal tract.

Compositions or matter for ocular administration are for placement in the lower conjunctival fromix from which the drug diffuses through a membrane over a seven day period at a constant rate. Such systems are described in *The United States Pharmacopeia/National Formulary*, USP23/NF18, 1995, p. 1949, United States Pharmacopeial Convention, Inc.

Compositions of matter for transdermal administration are also within the scope of the invention. Such systems are described in the *United States Pharmacopeia/National Formulary*, p. 1949, 1995.

Compositions of matter for rectal administration may be administered in the form of a suppository as disclosed in the *United States Pharmacopeia/National Formulatory*, p. 1948, 1995.

Compositions of, matter for pulmonary administration (by inhalation or aerosol) may be administered in the form of an aerosol spray using, for example, a nebulizer such as those disclosed in U.S. Pat. No. 4,624,251, issued Nov. 25, 1986, U.S. Pat. No. 3,703,173, issued Nov. 21, 1972, U.S. Pat. No. 3,561,444 issued Feb. 9, 1971 and U.S. Pat. No. 3,635,627 issued Jan. 13, 1971. The aerosol material is inhaled by the subject to be treated.

Other systems of aerosol delivery such as the pressurized metered dose inhaler (MDI) and the dry power inhaler as disclosed in Newman, S. P. in Aerosol and the Lung, Clark, S. V. and Davis, D. eds., pp., 197–224, Butterworthe, London, England, 1984, can be used when practicing the present invention.

Aerosol delivery systems of the type disclosed herein are available from numerous commercial sources including Sisons Corporation (Bedford, Mass.), Schering Corp. (Kenilworth, N.J.) and American Pharmacoseal Company (Valencia, Calif.).

The compositions of matter described herein may also be liquid preparations, for administration as a spray, drops, or syrups. The preferred diluent is water, in which the pharmaceutically active agent and ancillary agents, along with the phosphocholine surfactant are dispersed by any method usually employed for suspension or emulsification, such as ultrasonic treatment or stirring.

The pharmaceutical formulation or dosage forms of the present invention need not constitute an "effective amount" of the pharmaceutical agent for treating the various disorders as such effective amounts can be reached by administering a plurality of such formulations or dosage forms.

The present invention is further described below in specific examples which are intended to further describe the invention without limiting the scope thereof.

EXAMPLE 1

Preparation of Phosphocholine Surfactants and Related Compounds

According to the present invention, starting compounds which may be any one of a number of sterol compounds or fatty alcohols, may be converted to the corresponding phosphocholine conjugate using any methods that are know in the art. In one preferred embodiment, the hydrophobic alcohol is dissolved in a suitable anhydrous aprotic solvent, such as chloroform, tetrahydrofuran, or methylene chloride. 110 to 320 mol % of triethylamine is added and the reaction cooled in an ice/methanol bath. 100 to 200 mol % of 2-chloro-1,3,2-dioxaphospholane-2-oxide reagent (Aldrich) is added dropwise, and the reaction allowed to warm to room temperature over a period of 2 hours. Progress of the reaction is monitored by TLC (1:1 ethyl acetate:hexanes), and typically allowed to proceed for 12 to 24 hours.

Once the starting material is converted to the phosphorylated intermediate, the reaction mixture is washed with water to remove polar impurities from the immiscible organic solvent. The phosphorylated intermediate is isolated by the vacuum removal of the organic solvent, and dissolved in acetonitrile. The reaction is cooled in an ice/methanol bath, an excess of trimethylamine is condensed into the reaction vessel, and the reaction allowed to proceed for 24–72 hours at 60° C. At completion of the reaction, excess trimethylamine is removed by purging the reaction vessel with nitrogen and venting the gas through acidified water. The phosphocholine conjugate typically precipitates and is collected by filtration and washed with acetonitrile. This procedure will work for each of the 5 classes of surfactants disclosed herein.

REFERENCES CITED

U.S. PATENT DOCUMENTS

| | | |
|---|---|---|
| 5,747,066 | 5/1998 | Pittrof et al. |
| 4,837,023 | 6/1989 | Eibl |
| 5,439,669 | 8/1995 | Kaufman et al. |
| 5,703,063 | 12/1997 | Chasalow |
| 5,714,520 | 2/1998 | Jones et al. |

OTHER PUBLICATIONS

Lyte, M. et al. Cholesteryl-Phosphoryl-Choline in Lipid Bilayers. Chem. Phys. Lipids vol. 24, pp. 45–55 (1979).

Ayengar, N. K. N. et al. Effect of Two OH-Substituted Cholesterol Derivatives on Monolayer Condensation and Membrane Closure. Chem. Phys. Lipids vol. 25, pp. 203–208 (1979).

Jones, M. N. et al. Micelles, Monolayers, and Biomembranes. Wiley-Liss, N. Y. (1995).

We claim:

1. A pharmaceutical formulation comprising a pharmaceutically active agent, which is insoluble or sparingly soluble in water and a sterol phosphocholine surfactant of the formula:

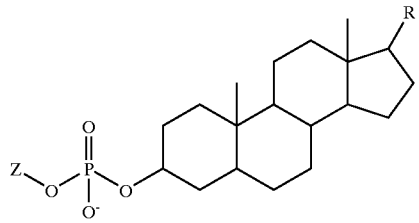

wherein R contains about 4 to 24 carbon atoms, may be saturated or unsaturated, and may be straight chain aliphatic or branched chain aliphatic group; and Z is selected from the group consisting of choline, ethanolamine, -methyl ethanolamine, N,N-dimethyl ethanolamine, serine, threonine, or tyrosine and a pharmaceutically acceptable carrier or diluent.

2. A pharmaceutical formulation comprising a pharmaceutically active agent which is insoluble or sparingly soluble in water, and a sterol phosphocholine surfactant of the formula:

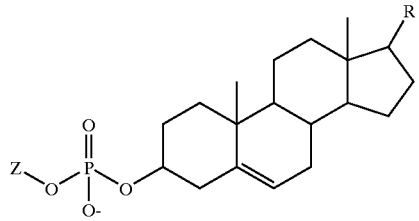

wherein R contains about 4 to 24 carbon atoms, may be saturated or unsaturated, and may be straight chain aliphatic or branched chain aliphatic group; and Z is selected from the group consisting of choline, ethanolamine, -methyl ethanolamine, N,N-dimethyl ethanolamine, serine, threonine, or tyrosine and a pharmaceutically acceptable carrier or diluent.

3. A pharmaceutical formulation comprising a pharmaceutically active agent which is insoluble or sparingly soluble in water, and a sterol phosphocholine surfactant of the formula:

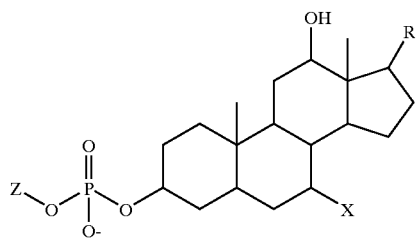

wherein R contains about 4 to 24 carbon atoms, may be saturated or unsaturated, and may be straight chain aliphatic or branched chain aliphatic group, and X=H or OH; and Z is selected from the group consisting of choline, ethanolamine, N-methyl ethanolamine, N,N-dimethyl ethanolamine, serine, threonine, or tyrosine and a pharmaceutically acceptable carrier or diluent.

4. A pharmaceutical formulation comprising a pharmaceutically active agent which is insoluble or sparingly soluble in water, and a sterol phosphocholine surfactant of the formula:

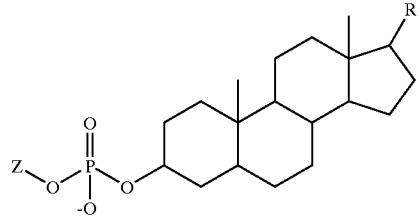

wherein R contains about 4 to 24 carbon atoms, may be saturated or unsaturated, and may be straight chain aliphatic or branched chain aliphatic group; and Z is selected from the group consisting of choline, ethanolamine, N-methyl ethanolamine, N,N-dimethyl ethanolamine, serine, threonine, or tyrosine and a pharmaceutically acceptable carrier or diluent.

5. A method comprising the oral, parenteral, rectal, nasal, ocular, transdermal, or pulmonary administration of the formulation of claim 1.

6. The pharmaceutical formulation of claim 1 which is for oral, parenteral, rectal, nasal, ocular, transdermal or pulmonary administration.

7. The pharmaceutical formulation of claim 2 which is for oral, parenteral, rectal, nasal, ocular, transdermal or pulmonary administration.

8. The pharmaceutical formulation of claim 3 which is for oral, parenteral, rectal, nasal, ocular, transdermal or pulmonary administration.

9. The pharmaceutical formulation of claim 4 which is for oral, parenteral, rectal, nasal, ocular, transdermal or pulmonary administration.

10. The formulation of claim 1 wherein the pharmaceutically active agent is for intravascular administration.

11. The formulation of claim 1 wherein the pharmaceutically active agent is selected from the group consisting of etoposide, paclitaxel, propofol and cyclosporin.

12. The formulation of claim 4 wherein the pharmaceutically active agent is for intravascular administration.

13. The formulation of claim 4 wherein the pharmaceutically active agent is selected from the group consisting of etoposide, paclitaxel, propofol and cyclosporin.

* * * * *